United States Patent
Hanna et al.

(10) Patent No.: US 6,505,133 B1
(45) Date of Patent: Jan. 7, 2003

(54) SIMULTANEOUS SIGNAL ATTENUATION MEASUREMENTS UTILIZING CODE DIVISION MULTIPLEXING

(75) Inventors: D. Alan Hanna, Boulder, CO (US); Mark A. Norris, Boulder, CO (US)

(73) Assignee: Datex-Ohmeda, Inc., Madison, WI (US)

(*) Notice: Subject to any disclaimer, the term of this patent is extended or adjusted under 35 U.S.C. 154(b) by 0 days.

(21) Appl. No.: 09/712,864

(22) Filed: Nov. 15, 2000

(51) Int. Cl.[7] ............................................. G06F 19/00
(52) U.S. Cl. ................................... 702/74; 702/79
(58) Field of Search ............................ 702/10, 69, 74, 702/79, 108, 110, 122, 124–126, 176–178, 783, 189, 193, 194, 196, 197; 600/309, 386, 310; 370/320, 535, 536, 203, 206; 375/316, 322, 329, 332, 346

(56) References Cited

U.S. PATENT DOCUMENTS

| | | | |
|---|---|---|---|
| 4,800,885 A | 1/1989 | Johnson ...................... 128/633 |
| 4,819,752 A | 4/1989 | Zelin .......................... 128/633 |
| 4,848,901 A | 7/1989 | Hood, Jr. ..................... 356/41 |
| 4,930,140 A | 5/1990 | Cripps et al. ................. 375/1 |
| 4,972,331 A | 11/1990 | Chance ....................... 364/550 |
| 5,122,974 A | 6/1992 | Chance ....................... 364/550 |
| 5,193,543 A | 3/1993 | Yelderman ................... 128/633 |
| 5,204,874 A * | 4/1993 | Falconer et al. ............. 370/209 |
| 5,277,181 A | 1/1994 | Mendelson et al. ......... 128/633 |
| 5,320,098 A | 6/1994 | Davidson .................... 128/630 |
| 5,343,818 A | 9/1994 | McCarthy et al. .......... 128/633 |
| 5,349,952 A * | 9/1994 | McCarthy et al. ............. 356/41 |
| 5,349,953 A * | 9/1994 | McCarthy et al. ........... 600/323 |
| 5,387,259 A | 2/1995 | Davidson .................... 128/630 |
| 5,460,182 A | 10/1995 | Goodman et al. .......... 128/664 |
| 5,766,127 A | 6/1998 | Pologe et al. ............... 600/310 |
| 5,769,791 A | 6/1998 | Benaron et al. ............ 600/473 |
| 5,772,597 A | 6/1998 | Goldberger et al. ........ 600/473 |
| 5,774,213 A | 6/1998 | Trebino et al. ............. 356/320 |
| 5,782,758 A | 7/1998 | Ausec et al. ................ 600/336 |
| 5,785,658 A | 7/1998 | Benaron et al. ............ 600/473 |
| 5,800,348 A | 9/1998 | Kaestle ....................... 600/322 |
| 5,805,583 A | 9/1998 | Rakib .......................... 370/342 |
| 5,807,261 A | 9/1998 | Benaron et al. ............ 600/473 |
| 5,891,022 A | 4/1999 | Pologe ........................ 600/323 |
| 5,891,024 A | 4/1999 | Jarman et al. .............. 600/323 |
| 5,919,134 A * | 7/1999 | Diab ........................... 600/323 |
| 5,921,921 A * | 7/1999 | Potratz et al. .............. 600/323 |
| 5,934,277 A | 8/1999 | Mortz ......................... 128/633 |
| 5,995,858 A | 11/1999 | Kinast ........................ 600/323 |
| 6,097,712 A * | 8/2000 | Secord et al. .............. 600/323 |
| 6,229,856 B1 | 5/2001 | Diab et al. .................. 375/316 |
| 6,269,267 B1 | 7/2001 | Brady et al. .................. 607/5 |

* cited by examiner

*Primary Examiner*—Marc S. Hoff
*Assistant Examiner*—Craig Steven Miller
(74) *Attorney, Agent, or Firm*—Marsh Fischmann & Breyfogle LLP (57) ABSTRACT

A pulse oximeter (100) includes two or more light sources (102) for transmitting optical signals through an appendage (103) of patient. The sources (102) are operated to transmit code division multiplexed (CDM) signals. That is, the sources (102) are driven by drives (104) in response to signals from a digital processing unit (116) such that the sources (102) are modulated using different code sequences. The code sequences are preferably non-periodic and may be orthogonal to one another. The use of such CDM signals provides certain advantages related to noise reduction.

24 Claims, 5 Drawing Sheets

SIMULTANEOUS SIGNAL ATTENUATION MEASUREMENTS UTILIZING CODE DIVISION MULTIPLEXING

FIELD OF THE INVENTION

The present invention relates in general to simultaneous signal attenuation measurement systems and, in particular, to the use of code division multiplexing in such systems to identify attenuation characteristics associated with individual signal components.

BACKGROUND OF THE INVENTION

Signal attenuation measurements generally involve transmitting a signal towards or through a medium under analysis, detecting the signal transmitted through or reflected by the medium and computing a parameter value for the medium based on attenuation of the signal by the medium. In simultaneous signal attenuation measurement systems, multiple signals are simultaneously transmitted (i.e., two or more signals are transmitted during at least one measurement interval) to the medium and detected in order to obtain information regarding the medium.

Such attenuation measurement systems are used in various applications in various industries. For example, in the medical or health care field, optical (i.e., visible spectrum or other wavelength) signals are utilized to monitor the composition of respiratory and anesthetic gases, and to analyze tissue or a blood sample with regard to oxygen saturation, analyte values (e.g., related to certain hemoglobins) or other composition related values.

The case of pulse oximetry is illustrative. Pulse oximeters determine an oxygen saturation level of a patient's blood, or related analyte values, based on transmission/absorption characteristics of light transmitted through or reflected from the patient's tissue. In particular, pulse oximeters generally include a probe for attaching to a patient's appendage such as a finger, earlobe or nasal septum. The probe is used to transmit pulsed optical signals of at least two wavelengths, typically red and infrared, to the patient's appendage. The transmitted signals are received by a detector that provides an analog electrical output signal representative of the received optical signals. By processing the electrical signal and analyzing signal values for each of the wavelengths at different portions of a patient pulse cycle, information can be obtained regarding blood oxygen saturation.

Such pulse oximeters generally include multiple sources (emitters) and one or more detectors. A modulation mechanism is generally used to allow the contribution of each source to the detector output to be determined. Conventional pulse oximeters generally employ time division multiplexing (TDM) signals. As noted above, the processing of the electrical signals involves separate consideration of the portions of the signal attributable to each of the sources. Such processing generally also involves consideration of a dark current present when neither source is in an "on" state. In TDM oximeters, the sources are pulsed at different times separated by dark periods. Because the first source "on" period, the second source "on" period and dark periods occur at separate times, the associated signal portions can be easily distinguished for processing.

Alternatively, pulse oximeters may employ frequency division multiplexing (FDM) signals. In the case of FDM, each of the sources is pulsed at a different frequency resulting in detector signals that have multiple periodic components. Conventional signal processing components and techniques can be utilized to extract information about the different frequency components.

In order to accurately determine information regarding the subject, it is desirable to minimize noise in the detector signal. Such noise may arise from a variety of sources. For example, one source of noise relates to ambient light incident on the detector. Another source of noise is electronic noise generated by various oximeter components. Many significant sources of noise have a periodic component.

Various attempts to minimize the effects of such noise have been implemented in hardware or software. For example, various filtering techniques have been employed to filter from the detector signal frequency or wavelength components that are not of interest. However, because of the periodic nature of many sources of noise and the broad spectral effects of associated harmonics, the effectiveness of such filtering techniques is limited. In this regard, it is noted that both TDM signals and FDM signals are periodic in nature. Accordingly, it may be difficult for a filter to discriminate between signal components and noise components having a similar period.

SUMMARY OF THE INVENTION

The present invention is directed to a simultaneous signal attenuation measurement system employing code division multiplexing (CDM). The invention allows for analysis of a multiplexed signal to distinguish between two or more signal components thereof based on codes modulated into the signal components. The CDM codes are nonperiodic thereby facilitating various processing techniques for distinguishing the signals of interest from noise or other interference. Moreover, the invention allows for a variety of hardware and processing options that may reduce costs, simplify system operation and improved accuracy of the attenuation measurements.

According to one aspect of the present invention, codes are modulated into the transmitted signals of a signal attenuation measurement system. The system includes at least two signal sources (e.g., having different wavelengths) that are pulsed by source drives to a medium under analysis. One or more detectors receive the first and second signal from the medium (e.g., after transmission through or reflection from the medium) and output a composite signal reflecting contributions corresponding to each of the transmitted source signals. The detector signal is thus a multiplexed signal composed of at least two signal components. In accordance with the present invention, the source drives are operated to modulate each of the source signals based on a code. For example, each drive may pulse a corresponding one of the signal sources between a high output or "on" state and a low value or "off" state. It will be appreciated that, depending on the sources employed, substantial photonic energy may be transmitted in the nominal "off" state. Accordingly, in the context of the source signals, a code may be conceptualized as a bit stream of "0s" and "1s", where "0" corresponds to an off state, "1" corresponds to an on state, and the bit length corresponds to a base unit of time that generally reflects the shortest pulse length utilized in driving the sources.

The codes define source signals that have nonperiodic characteristics. That is, due to the codes, there is at least a component of each source signal that is not described by a regularly repeating temporal pattern. As will be understood from the description below, however, the codes themselves may be concatenated in the source signal and a periodic modulating signal may carry the coded signal.

A number of preferred characteristics have been identified for the codes. Among these are:

1. the codes for the different sources are preferably mathematically orthogonal;
2. the numbers of 1s and 0s in a code should be about the same;
3. the distribution of 1 s and 0s within a code should be fairly even; and
4. the distribution of transitions between 1s and 0s within a code should be fairly even.

These preferences and some bases therefor are described in detail below. The codes utilized in accordance with the present invention preferably have one or more of these characteristics and, more preferably, have all of the noted characteristics.

According to another aspect of the invention, a detector signal is processed in a signal attenuation measurement system to demultiplex the detector signal and extract component information therefrom based on nonperiodic codes. In particular, the detector signal is first processed to provide a processed signal for demultiplexing and the processed signal is then demultiplexed using at least one coded demultiplexing signal that includes a series of values defining a nonperiodic code. Information is thereby obtained regarding first and second signal components of the detector signal. This information can be utilized in an attenuation analysis to determine an attenuation related parameter of a medium under analysis.

The initial processing of the detector signal may include various processing steps and components depending on the specific application and implementation. For example, where the detector signal is an analog signal, initial processing may involve analog to digital conversion. Preferably, such conversion is implemented using a fast analog to digital converter that digitally samples the detector signal multiple times per source cycle. Such a convertor in combination with processing techniques enabled by code division multiplexing allows for improved measurement accuracy and hardware implementation options for certain attenuation measurement applications. The initial processing may further or alternatively include signal filtering to reduce undesired components, signal amplification including, e.g., DC rectification to remove or avoid amplifying DC or low frequency components especially in the case of DC coupled sources, and/or other signal enhancement processing.

Preferably, the demultiplexing process involves the use of a unique demultiplexing signal for each signal component of interest, e.g., corresponding to each signal source. In this regard, the same codes used for modulating the source signals may be used to demodulate the detector signal. However, for mathematical convenience, the demodulating codes may be conceptualized as a series of −1s and +1s rather than 0s and 1s as discussed above in relation to the modulating codes. The coded demodulating signal may be filtered to compensate for certain wave shape distortions resulting from bandwidth limitations and non-linearities and/or to reduce response at certain frequencies. In addition, the codes may be pre-computed to reduce storage and processing requirements.

BRIEF DESCRIPTION OF THE DRAWINGS

For a more complete understanding of the present invention and further advantages thereof, reference is now made to the following detailed description, taken in conjunction with the drawings, in which.

DETAILED DESCRIPTION OF THE INVENTION

The code division multiplexing system of the present invention may be used in a variety of signal attenuation measurement devices. In the following description, the invention is set forth in the context of a pulse oximeter used to measure blood oxygen saturation or related blood analyte values. As will be described below, the invention has particular advantages in the context of pulse oximetry including allowing for improved noise reduction and oximeter component options. However, while pulse oximetry represents a particularly advantageous application of the present invention, it will be understood that various aspects of the present invention are more broadly applicable in a variety of simultaneous signal attenuation measurement contexts.

In the following description, the pulse oximetry environment is first described with reference to a specific pulse oximeter embodiment. Thereafter, specific implementations of the code division multiplexing system of the present invention are described.

Figure 1:
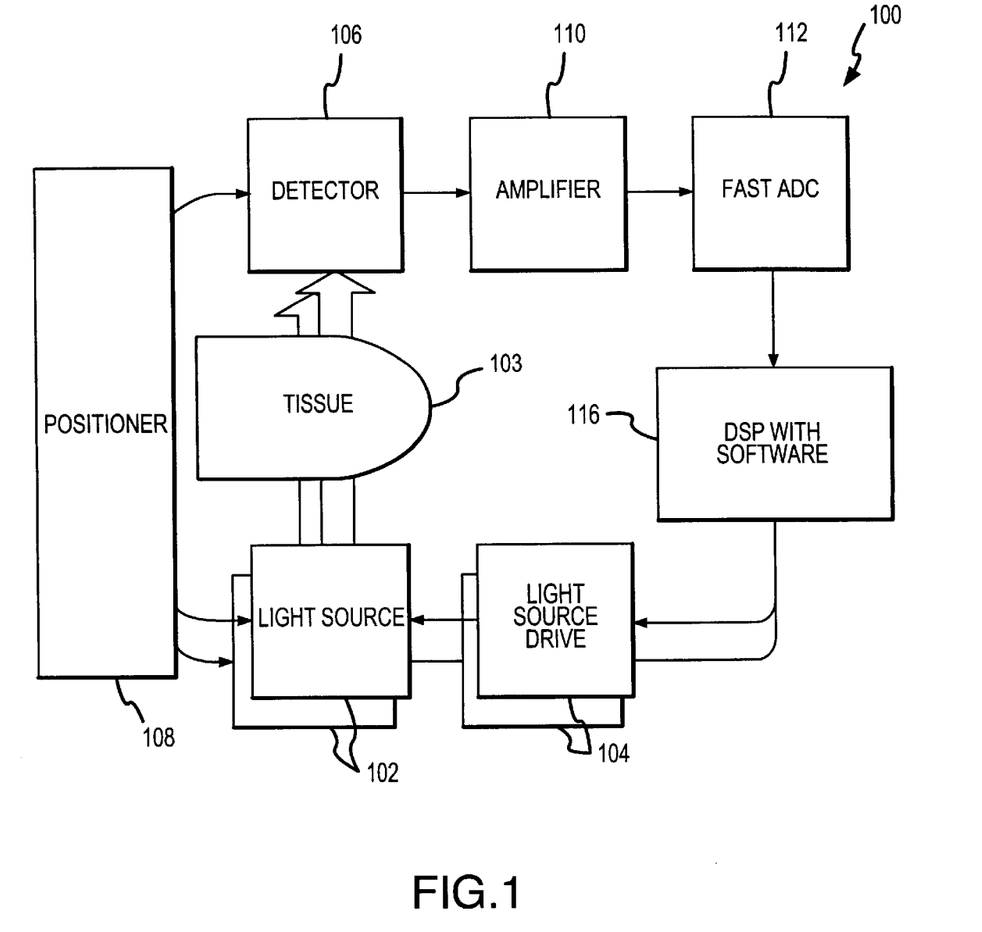
FIG. 1 is a schematic diagram of a pulse oximeter in connection with which the present invention may be implemented.

Referring to FIG. 1, a pulse oximeter in accordance with the present invention is generally identified by the reference numeral 100. The pulse oximeter 100 includes two or more light sources 102 for transmitting optical signals through an appendage 103 of a patient. In the illustrated embodiment, two light sources 102 are shown. For example, the light sources 102 may include a red LED and an infrared LED. The light sources 102 are driven by light source drives 104 in response to drive signals from a digital signal processing unit 116. In the illustrated embodiment, as will be described in more detail below, the signals from the light sources 102 are modulated using different code sequences. For example, the source drive 104 associated with the red light source 102 may pulse the red light source in accordance with a first code sequence and the light source drive 104 associated with the infrared light source 102 may pulse the infrared light source 102 in accordance with a second code sequence different from the first code sequence. It will be appreciated that such a multiplexing system does not result in a periodic signals such as in the case of time division multiplexed or frequency division multiplexed signals. In particular, the pulsing of the sources 102 between "on" and "off" states does not define a regularly repeating waveform. It should also be noted that although the following description references "on" and "off" cycles for each of the sources 102, in reality, the optical signals associated with each source 102 do not define an ideal square wave. For example, substantial photonic energy is emitted even in the "off" state in the case of DC coupled sources. In addition, the intensity transmitted by each of the sources 102 can vary substantially within an "on" cycle. The ability to recognize and address such non-ideal characteristics is an advantage of the present invention.

The optical signals transmitted by the light sources 102 are transmitted through the patient's appendage 103 and impinge upon a detector 106. In this regard, a positioner 108 provides for proper alignment of the sources 102 and the detector 106. Various different types of positioners 108 are available depending, for example, on the appendage to be irradiated and on the patient (e.g. different positioners 108 may be provided for neonatal and adult patients). One typical type of positioner 108 is provided in the form of a clothespin-like clamp which engages a patient's fingertip. When the positioner 108 is engaged on the patient's fingertip, the light sources are positioned on one side of the patient's finger and the detector 106 is positioned on the opposite side in alignment with the light sources so as to receive the optical signals transmitted through the patient's finger. It will be appreciated that, in alternative implementations, a reflective pulse oximeter may be employed whereby the sources and detector are located on the same side of the patient's appendage so as to receive optical signals reflected back from the patient's tissue.

The detector 106 receives the optical signals transmitted through the patient's appendage 103 and provides an analog signal representative of the received optical signals. In the illustrated embodiment, the detector 106 outputs an analog current signal where the magnitude of the current at any given time is proportional to the cumulative intensity of the received optical signals. The detector signal in the illustrated embodiment is then processed by an amplifier circuit 110. The amplifier circuit may serve a number of functions. First, the illustrated amplifier circuit is operative for converting the input analog current signal from the detector 106 into an analog voltage signal. The amplifier circuit 110 may also be operative for subtracting certain DC and low frequency components from the detector signal. For example, one DC component which may be subtracted from-the detector signal relates to photonic energy transmitted by the sources 102 during "dark periods." That is, as noted above, practical source implementations generally transmit a signal of some intensity even during off periods. In addition, low frequency ambient light may be subtracted from the detector signal. The amplifier circuit 110 may also filter out certain high frequency electronic noise and provide other signal processing functionality.

The amplifier circuit 110 outputs an analog voltage signal which is representative of the optical signals (or frequency division multiplexed signal) from the sources 102. This analog voltage signal is received by a fast A/D converter 112 which samples the analog voltage signal to generate a digital voltage signal which can be processed by the digital signal processing unit 116. In particular, the converter 112 preferably takes multiple digital samples per cycle of each of the sources 102. That is, the sampling rate of the converter 112 is sufficiently fast to take multiple samples, for example, at least about 20 samples per "on" period of each of the sources 102. Such multiple sampling per cycle allows the oximeter to track the shape of the detector signal, to allow for reduced noise processing of the resulting digital signal and to identify phase components of interest within a signal cycle. Multiple samples per dark period are also obtained. It will thus be appreciated that the values output by the converter 112 are not integrated or aggregate values corresponding to a source cycle period or dark period, but rather, are substantially instantaneous values reflecting the detector signal at a moment within a cycle.

The digital signal processor 116 implements a number of functions. Of particular importance to the present invention, and as will be described in more detail below, the processor 116 includes a demultiplexer module, i.e., the processor executes a variety of demultiplexing software/logic functions including generating or otherwise obtaining a coded demultiplexing signal corresponding to each signal component associated with each source, processing the composite signal using each of the demultiplexing signals to obtain a set of values reflecting the contribution of each source, and using these value sets to obtain instantaneous intensity related values for each of the sources. The processor 116 also includes a parameter calculation module for calculating blood oxygen saturation or related parameter values using known algorithms.

Figure 2:
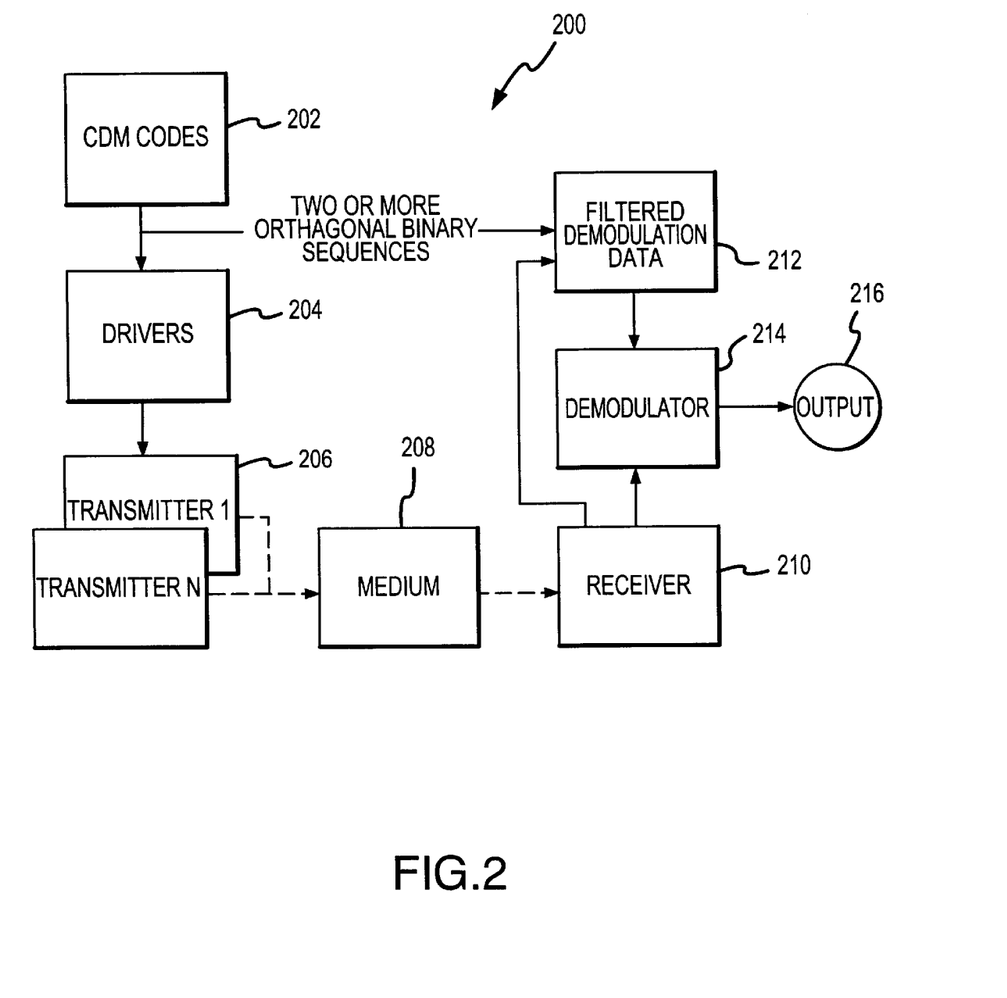
FIG. 2 is a block diagram illustrating a code division multiplexing system in accordance with the present invention.

FIG. 2 illustrates a code division multiplexing system 200 that can be implemented in the pulse oximeter 100 of FIG. 1 in accordance with the present invention. The system 200 includes a code module 202 for providing codes that are used to modulate the sources and demultiplex the detector signal. A number of preferred criteria have been identified with respect to the codes employed. First, these codes are preferably selected, relative to one another, in a manner that allows for processing so as to accurately distinguish the contributions of each of the sources. In this regard, the codes may be substantially orthogonal to reduce any interference between the two signal components, or "channels", corresponding to the two different sources and their wavelengths/spectral composition. As noted above, the codes may be conceptualized as binary sequences. In the context of the sources it is convenient to conceptualize the code sequence in terms of 0 and 1 bits corresponding to the off or low output state, on the one hand, and the on or high output state on the other. In the case of the demultiplexing signal, the bits are conceptualized as $-1$ and $+1$ for mathematical convenience. In the following discussion, the $-1$ and $+1$ convention is used. The following sequences illustrate the concept of code orthogonality as well as the mathematical convenience of +1s and $-1$s for a particular processing technique:

$$\begin{array}{rrrr} -1 & 1 & 1 & -1 \\ -1 & -1 & 1 & 1 \\ \hline 1 & -1 & 1 & -1 \end{array}$$

The first line above is a first code sequence and the second line above is a second code sequence. These two code sequences are orthogonal in that half the time that the bit value of the first code is $-1$, the bit value of the second code is $-1$ and vice versa. The other half of the time the bit values are opposite. A similar relationship holds for bit values of 1. The third line above is the bit-by-bit product of the first two code sequences. Because the corresponding bits of the codes are the same half of the time (producing a product of $+1$) and different the other half of the time (producing a product of $-1$), the sum of the bits in the third line above is 0. By contrast, the sum of the products of two identical codes would be equal to the number of bits in the code. As will be described below, this property facilitates isolation of the portion of the multiplexed detector signal attributable to each of the sources and obtainment of a value indicative of the intensity of that received signal at a given time or time period.

For example, the use of the following eight code segments in equal numbers will allow for generation of a number of suitable orthogonal code sequences:

```
-1 -1 -1 -1
-1 -1  1  1
-1  1 -1  1
-1  1  1 -1
 1 -1 -1  1
 1 -1  1 -1
 1  1 -1 -1
 1  1  1  1
```

It will be observed that these four bit segments include even numbers of −1s and/or +1s allowing for generation of codes based on combinations of these segments that are orthogonal as discussed above. Similar segments of different bit lengths may be used as a basis for generating orthogonal code sequences.

In addition to orthogonality, preferred codes for the illustrated implementation of the invention have a substantially equal number of +1s and −1s. In this manner, introduction of a DC offset is avoided as the code value integrates to zero over relevant intervals.

A further preferred code criterion is that the distribution of +1s and −1s in a code sequence should be relatively even. Most preferably, the numbers of +1s and −1s should be the same in each half of the pattern, each quarter of the pattern, each eighth of the pattern, etc., as far as practicable. Such spreading out of the +1s and −1s in a code sequence reduces the likelihood that low frequency noise will interfere with measured values.

Additionally, it is preferred that the transitions from −1 to +1 and vice versa be substantially evenly distributed in a code sequence so as to provide signals having similar energies. In this regard, it is preferable that the code can be divided into an integer number of segments where the number of transitions in each segment is substantially the same.

The codes can be generated according to the output of a random number generator, by an explicit algorithm, or by a stored series of values. In the case of a random number generator or explicit algorithm process, one or more of the criteria above can be applied by logic running on the digital signal processing platform at run time. With stored values, the criteria can be applied at run time or at the time the codes are generated. As discussed below, in one preferred implementation, the codes are pre-generated and stored to reduce processing/storage resource requirements. The codes can then be concatenated in generation of the drive signals.

Figure 3:
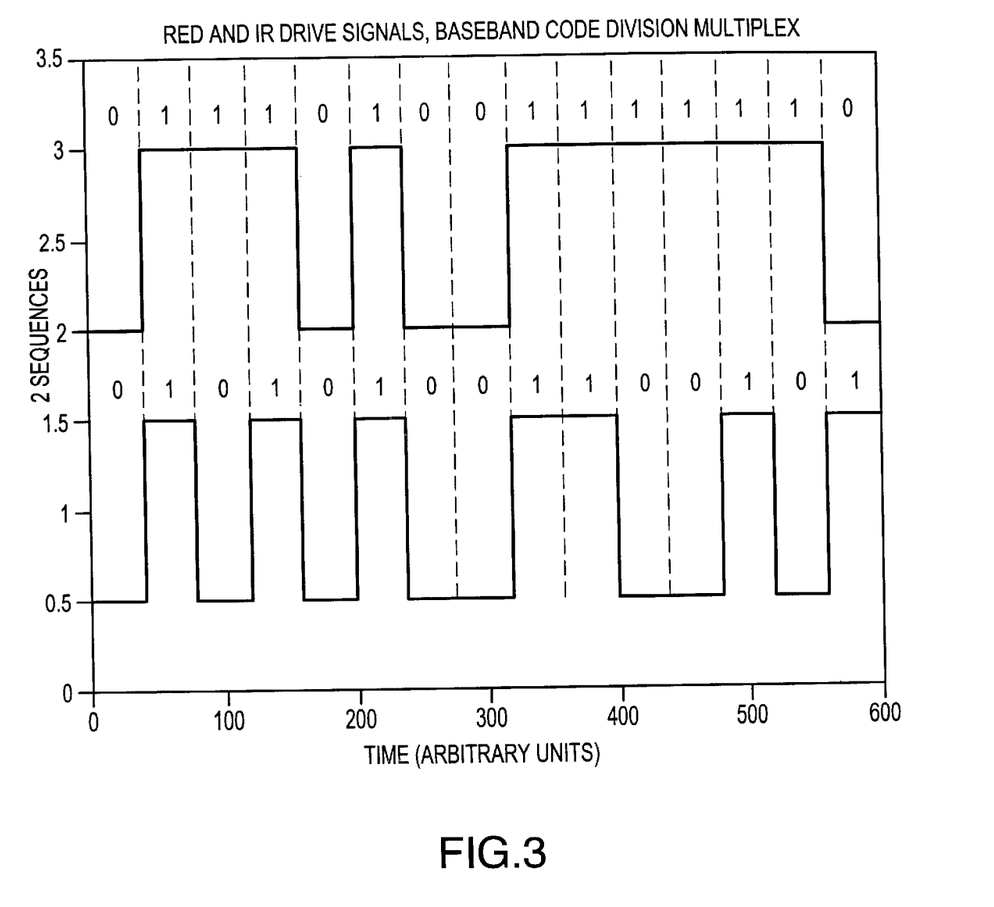
FIG. 3 illustrates two drive signals reflecting codes that may be used in the code division multiplexing system of the present invention.
Figure 4:
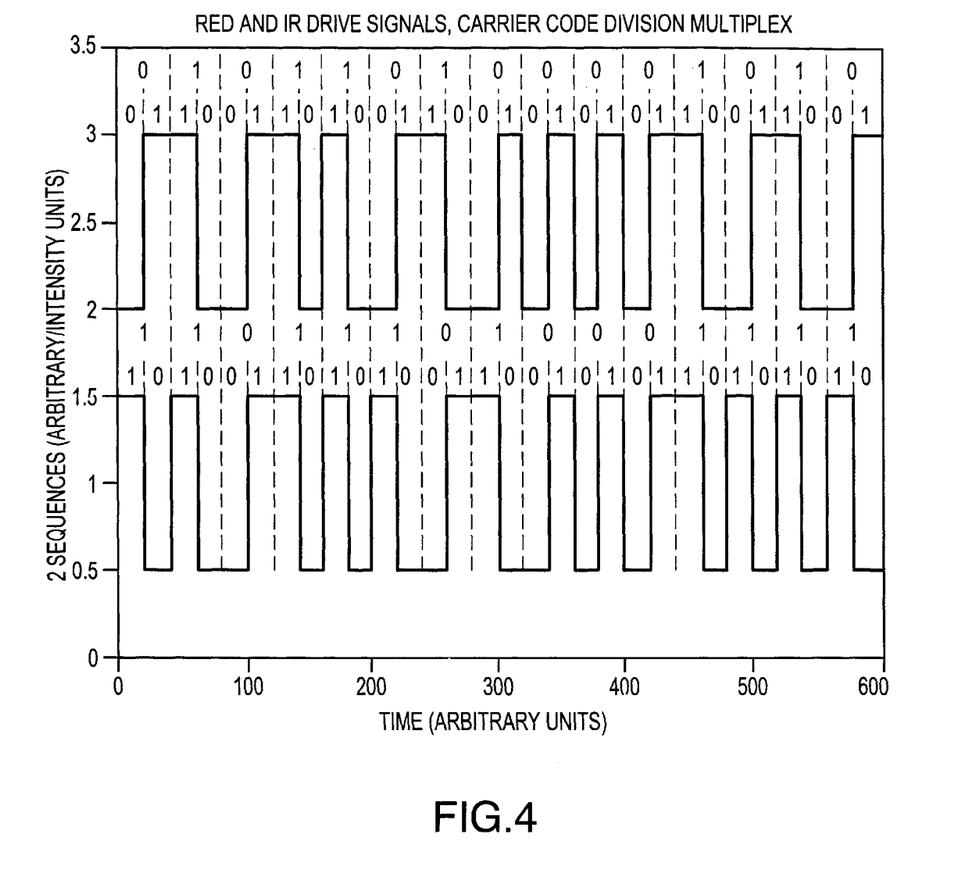
FIG. 4 illustrates two drive signals, reflecting codes transmitted using a carrier wave in accordance with the present invention.

These CDM codes are used by the drivers 204 for the respective sources 206 to encode or modulate the signals transmitted by the sources 206. Such encoded signals are generally illustrated in FIGS. 3–4. For purposes of illustration, FIGS. 3–4 show idealized square waves. It will be appreciated, however, that practical implementations may include waveforms that are somewhat distorted.

FIG. 3 illustrates two code sequences that may be transmitted by two respective sources during a given time period. It will be observed that the illustrated sources are pulsed between an on or high state (+1) and an off or low state (−1). The shortest time period of these states is taken to be a bit length. The resulting code sequences are reproduced above the signal waveforms in FIG. 3. The signals are labeled red and infrared corresponding to two channels commonly used in pulse oximetry. Additional channels or alternative channels may be utilized in accordance with the present invention.

FIG. 4 illustrates another two code sequences. In this case, the code sequences are further modulated using a carrier code. In this case, a 10 carrier pair is used to transmit a +1 code bit and a 01 carrier pair is used for a 0 code bit. The corresponding carrier pairs and associated code bit values for each code sequence are shown in FIG. 4. Such carrier code modulation has a number of advantages in the illustrated implementation. First, such modulation simplifies the process of satisfying the above noted code criteria as such criteria can be satisfied by the modulated code sequences rather than the base code sequences. In this regard, since each code bit is half 0 and half 1 and includes one transition, the transmitted code will automatically satisfy all of the above noted criteria except for orthogonality. The preferred code selection process therefore reduces to satisfying orthogonality.

Additionally, the carrier code takes the coded signal further away from DC or low frequency interference. By using higher frequency carriers (e.g., multiple carrier pairs per code bit), the resulting signal can be taken further away from DC or low frequency interference so that 1/f noise and power line noise (e.g., ambient light) have a reduced impact on the desired measurements. These higher frequency carriers produce nulls (noise minima) for several harmonics above the carrier frequency. By appropriate selection of the carrier frequency, these nulls can be used to ease anti-aliasing requirements.

Referring again to FIG. 2, the resulting signals transmitted by the sources 206 travel through the medium 208 in the illustrated embodiment. In this case, the medium may be, for example, a patient's finger, ear lobe or nasal septum. Alternatively, in the case of a reflective oximeter, the signal portions reflected from the medium may be detected to obtain information about the medium.

The signals are received by one or more detectors 210 that provide an electrical detector signal proportional to the received optical signal. Such a signal may be an analog current signal. In the illustrated embodiment, a single detector 210 receives the signals from both sources 206, thereby reducing components and costs as is desirable, particularly when the detector 210 is provided as part of a disposable or short lifespan probe. Accordingly, the detector signal is a composite signal including contributions from each of the sources 206. As discussed above, the detector signal may be processed by an amplifier circuit and an analog to digital circuit that are not shown in FIG. 2.

In particular, the amplifier circuit outputs an analog voltage signal which is representative of the optical signals (or code division multiplexed signal) from the sources. This analog voltage signal is received by a fast A/D converter which samples the analog voltage signal to generate a digital voltage signal which can be processed by the digital signal processing unit. The converter 112 takes multiple digital samples per time period corresponding to a code value or value of the carrier wave. That is, the sampling rate of the converter is sufficiently fast to take one or more samples and, more preferably at least about 3 samples and, even more preferably at least about 20 samples per "on" or "off" period of each of the sources 102. Such multiple sampling per cycle allows the oximeter to track the shape of the detector signal, to allow for reduced noise processing of the resulting digital signal, to reduce the required A/D converter word length and to identify phase components of interest within a signal cycle. In one implementation, information regarding the shape of the signal may be used in filtering the demodulating signal as discussed below. The code modulated composite signal may be sampled by the converter, for example, at a frequency of about 41,667 Hz. It will thus be appreciated that the values output by the converter 112 are not integrated or aggregate values corresponding to a source cycle period or dark period, but rather, are substantially instantaneous values reflecting the detector signal at a moment within a cycle. The result, in the illustrated embodiment, is that the detector signal as transmitted to the demodulator 214 is a series of digital values where each digital value corresponds to an intensity of the cumulative signals received by the detector at a given time or short time period.

In addition to this digital detector signal, the demodulator 214 also receives filtered demodulation data from demodulation signal module 212. The demodulation data is used to extract, from the composite code division multiplexed detector signal, information regarding the contribution to that composite detector signal from each of the sources. Generally, the demultiplexing process involves processing the composite detector signal using the first code associated with the first source to obtain received intensity information for the first source and processing the composite detector signal using the second code associated with the second source to obtain received intensity information for the second source. In particular, each such demultiplexing signal is generally composed of a series of concatenated code sequences corresponding to the drive signal for that source. The demultiplexing signal is synchronized to the drive signals (e.g., by reference to a common clock or based on a feed forward signal from the analog to digital converter) so that corresponding bits of the detector signal and demultiplexing signal are co-processed. The detector signal can then be demultiplexed by taking the bitwise product of the detector signal and demultiplexing signal for a sampling period (e.g., a short portion of a patient's pulse cycle) to obtain a demultiplexed binary sequence. This demultiplexed binary sequence can then be integrated to obtain a value indicative of the intensity of the detected signal portion attributable to the corresponding source. Such values form the output 216 that is transmitted to a parameter calculation module that executes any of various well-known algorithms for determining oxygen saturation or related parameter values based on signal attenuation or the detected intensity values.

The illustrated demodulation signal module 212 performs a number of functions in generating the demodulation signals. First, as noted above, the module 212 concatenates each of the codes to obtain the base demultiplexing signal form. This signal form is also filtered by the module 212 to obtain an improved demultiplexing signal. In this regard, the demodulation data may be filtered to compensate for signal distortion. Specifically, the discussion above has assumed idealized waveforms. In reality, due to bandwidth limitations and nonlinearities of the various components, the transmitted code is distorted to an extent by the transmission and receiving systems. If these distorted shapes were processed using idealized demultiplexing data, the effects of distortion could have a substantial impact on the resulting measurements. In the illustrated embodiment, the distorted wave shapes are detected by the analog to digital converter and used to filter the demodulation data so that, to a significant extent, the distortion effects are canceled out during demultiplexing and do not affect the resulting calculations. This maximizes signal strength and minimizes channel to channel crosstalk. It will be appreciated that these advantages result from the use of a fast A/D converter in conjunction with code division multiplexing. That is, the ability to represent each code bit of the detector signal and corresponding demultiplexing signal as a stream of multiple digital value allows for compensation relative to distortion of a waveform corresponding to a code bit.

The module 212 can also perform filtering to dampen or eliminate response at particular frequencies. For example, an expected source of noise is related to power line frequencies and harmonics thereof that modulate ambient light and certain electronic noise. The effects of such noise can be reduced, just as channel to channel crosstalk is minimized, by selecting the demodulation values so that processing the detector signal using the demodulation values tends to pass or amplify the desired components and block or de-emphasize the undesired components. That is, the demodulation signal can be modulated with a signal component that has a degree of orthogonality relative to the signal components representing the targeted noise. In this regard, the demodulating signals can be filtered with notch filters at the power line frequency and harmonics thereof to reduce interference. In addition, the demodulation signals may be high pass filtered to reduce response at noisier lower frequencies and low pass filtered to avoid aliasing problems. More generally, it will be appreciated that the demodulation signal may be filtered, modulated or otherwise processed in a variety of ways to more fully discriminate the signal component of interest from crosstalk, noise, distortion or other interference.

The code sequence is repeated in the demodulation signal. filtering effects such as noted above are also generally repeating, e.g., on a periodic basis. Accordingly, the demodulation signal is generally composed of a repeating series of values that can be stored (once or periodically based on feedback/feedforward data) and need not be computed on the fly. Preferably, the filtered demodulation sequence is pre-computed and stored. More preferably, only a portion of the overall sequence is stored. That is, after perhaps only a few bits, the sequence is similar to previously transmitted data. For many codes, it has been found that storing and concatenating only 3 to 5 bits results in crosstalk between channels of −140 db, even in severely band limited systems. Thus, storage and processing resource requirements can be minimized.

The system described above including wavelength division multiplexing, carrier based codes and a fast analog to digital converter, has a number of additional advantages. Using the carrier-based codes permits use of AC coupled transmitters and receivers. Such AC coupled transmitters and receivers may be advantageous in that they can reduce the DC offset of the detector signal. Because such DC components tend to be substantially larger than the AC signal of interest, saturation or reduced dynamic range is a concern. This can be avoided by using AC coupled transmitters and receivers. Even when the transmitter and receiver are of the DC type, the front-end amplifier may be AC coupled or use DC restoration as discussed above to reduce DC offset. Also, saturation and reduced dynamic range can be avoided by using a high resolution analog to digital converter, e.g., a 16 bit or greater converter.

The system described above may also use on/off transmitters or analog transmitters with on/off drivers to reduce costs. The on/off transmitters transmit extra power in the frequencies above the fundamental. If anti-aliasing filters are used, the efficiency of the system is lower. When anti-aliasing filters are not used, the system must have substantially greater bandwidth than is required for proper reception of the code. However, the losses due to on/off transmission are offset by the simplicity of the drive.

Figure 5:
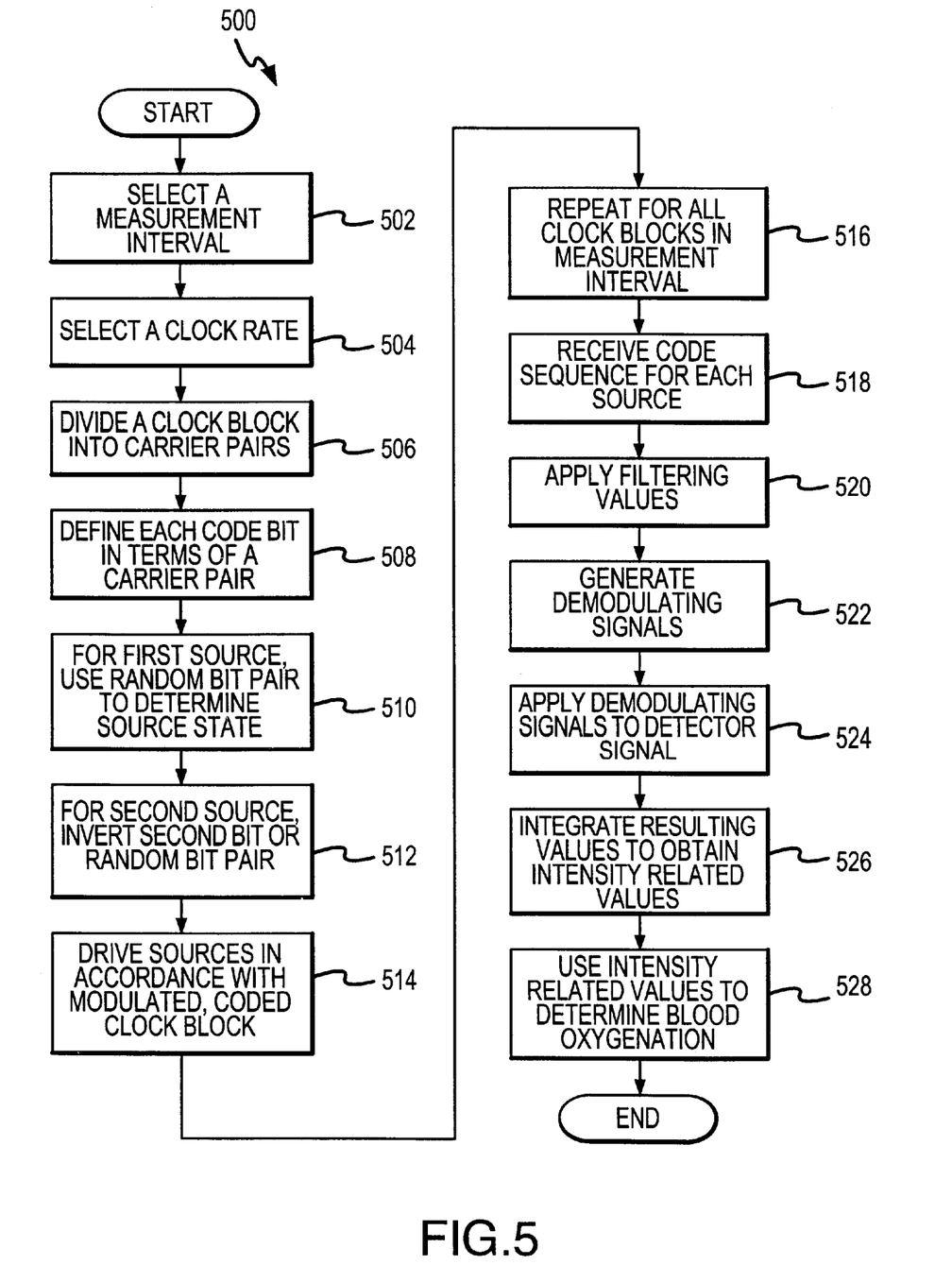
FIG. 5 is a flowchart illustrating a code division multiplexing process in accordance with the present invention.

The code division multiplexing process of the present invention can be summarized by reference to the flowchart of FIG. 5. The illustrated process 500 sets forth a specific example in the context of a two source pulse oximetry system where the codes are determined based on the output of a random number generator. It will be appreciated that various aspects of the methodology are more broadly applicable to alternative pulse oximetry implementations and other signal attenuation measurement environments.

The process 500 is initiated by selecting (502) a measurement interval. this will be the minimum time interval for which light intensity measurements can be obtained. Once the measurement interval is obtained, a clock rate is selected (504) for light source switching. This will be the minimum time for which any source can be turned on or off. The measurement interval and clock rate are preferably chosen so that, for a system with M light sources, each measurement interval has an integer number of clock blocks where each block has $2^M$ clocks. In the case of two sources, the measurement interval preferably has an integer number of clock blocks each having 4 clocks.

The process continues by dividing (506) each clock block into carrier pairs. Thus, in the case of the illustrated embodiment, a clock block is divided into two carriers pairs where each carrier pair defines a code bit. That is, each clock block includes four clocks or two code bits. An integer number of such clock blocks is included within each measurement interval. In addition, each code bit is defined (508) in terms of a carrier pair. Thus, for example, a code bit "1" may be defined as a carrier pair "10." A code bit of "0" may be defined as a carrier pair of "01."

The output of a random bit generator may be used (510) to determine the state of the first source. Thus, for example, if the random bit generator outputs a bit pair of "00," this may be modulated as a "0101" for purposes of driving the first source. For the second source, the second bit of this random bit pair is inverted (512). That is, the second source drive is encoded as "01." It will be appreciated that this bit pair is orthogonal to the bit pair used to drive the first source. The 01 code of the second source is modulated as "0110" in terms of the carrier pairs.

The sources are then driven (514) in accordance with the modulated, coded clock blocks. Specifically, in the case of the above-noted example, the first source is driven to transmit 0101 during the first clock block while the second source is driven to transmit 0110. This process is then repeated (516) for all clock blocks in a measurement interval.

On the receiver side, the demultiplexing module receives (518) the corresponding code sequence for each source. The module then applies (520) filtering values to these code sequences and generates (522) demodulating signals. These demodulating signals are applied (524) to the detector signal to produce a stream of values corresponding to the contributions of each of the sources. These values are then integrated (526) to obtain intensity related values which can then be used (528) to determine blood oxygen saturation or related parameter values.

Although the present invention has been described in several embodiments, various changes and modifications may be suggested to one skilled in the art. It is intended that the present invention encompass such changes and modifications that fall within the scope of the appended claims.

What is claimed is:

1. A method for use in operating a signal attenuation measurement device, the measurement device including a source system for generating first and second signals and for transmitting the first and second signals to a medium that attenuates the signals, a detector system for receiving first and second received signals from the medium and for providing a composite detector signal based on the first and second received signals, and a parameter module for determining an attenuation related parameter regarding the medium based on the detector signal, said method comprising:

processing the detector signal to provide a processed signal for demultiplexing, said processed signal including information regarding the first and second signals; and code division demultiplexing said processed signal using at least one coded demultiplexing signal, said at least one coded demultiplexing signal including a series of values defining a non-periodic code such that said demultiplexing of said processed signal using said at least one coded demultiplexing signal yields demultiplexed information corresponding to each of said first and second signals; wherein said demultiplexed information is used by the parameter module for determining the attenuation related parameter regarding the medium.

2. The method as claimed in claim 1, wherein the medium is a tissue of a patient, and the attenuation related parameter is one of a blood oxygen saturation value and a blood analyte value.

3. The method as claimed in claim 1, wherein said processed signal is an analog signal and the processing comprises converting at least a portion of the processed signal into a series of digital values.

4. The method as claimed in claim 1, wherein each of said first and second signals includes high value time periods and low value time periods and said processing of the detector signal comprises digitally sampling said detector signal multiple times within a time period corresponding to one of said high value and low value time periods of one of said first and second signals.

5. The method as claimed in claim 1, wherein said processing of the detector signal comprises filtering the detector signal to remove a selected frequency component.

6. The method as claimed in claim 1, wherein said demultiplexing comprises first processing said processed signal using a first coded demultiplexing signal corresponding to said first signal and second processing said processed signal using a second coded demultiplexing signal corresponding to said second signal.

7. The method as claimed in claim 6, wherein said first coded demultiplexing signal comprises a concatenation of a first code and said second coded demultiplexing signal comprises a concatenation of a second code.

8. The method as claimed in claim 7, wherein said first code is substantially orthogonal to said second code.

9. The method as claimed in claim 8, further comprising modulating at least one of said codes into a carrier signal.

10. The method as claimed in claim 9, wherein said carrier signal includes a plurality of values for expressing one of a high value and a low value for individual segments of said codes.

11. The method as claimed in claim 8, wherein each of said codes is computed prior to transmission of said first and second signals.

12. The method as claimed in claim 7, wherein each of said first and second codes is a digital code comprising a series of high and low values.

13. The method as claimed in claim 12, wherein each of said first and second codes includes said high and low values in substantially equal temporal portions.

14. The method as claimed in claim 12, wherein, within each of said first and second codes, said high values and low values are distributed so that there is substantially the same number of instances of high values and low values in the first and second temporal halves thereof.

15. The method as claimed in claim 12, wherein, within each of said first and second codes, said high values and low values are distributed so that there is substantially the same number of instances of high values and low values in the each temporal quarter thereof.

16. The method as claimed in claim 12, wherein, within each of said first and second codes, transitions between said high values and low values are distributed so that there is substantially the same number of transitions between high values and low values in the first and second temporal halves thereof.

17. The method as claimed in claim 12, wherein, within each of said first and second codes, transitions between said high values and low values are distributed so that there is substantially the same number of transitions between high values and low values in each temporal quarter thereof.

18. The method as claimed in claim 6, wherein said demultiplexing comprises filtering each of said first and second coded demultiplexing signals.

19. The method as claimed in claim 18, wherein said filtering comprises monitoring wave shapes corresponding to said first and second signals and using said wave shapes to filter said first and second coded demltiplexing signals.

20. The method as claimed in claim 18, wherein said filtering comprises filtering said first and second coded demultiplexing signals to remove an undesired frequency component.

21. The method as claimed in claim 20, wherein said filtering to remove undesired frequency components includes precomputing at least a portion of each of the first and second coded demultiplexing signals to effect removal of said undesired frequency component.

22. The method as claimed in claim 1, further comprising using first and second coded modulating signals to drive the source system.

23. The method as claimed in claim 1, further comprising AC coupling at least one of the source system and the detector system.

24. The method as claimed in claim 1, further comprising using on/off transmitters in said source system to generate said first and second signals.

* * * * *